US010799639B2

(12) United States Patent
Wei

(10) Patent No.: US 10,799,639 B2
(45) Date of Patent: Oct. 13, 2020

(54) SYRINGE TYPE MEDICATION DELIVERY DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 306 days.

(21) Appl. No.: 15/910,156

(22) Filed: Mar. 2, 2018

(65) Prior Publication Data

US 2018/0250474 A1   Sep. 6, 2018

Related U.S. Application Data

(60) Provisional application No. 62/467,065, filed on Mar. 3, 2017.

(51) Int. Cl.
*A61M 5/315* (2006.01)
*A61M 5/31* (2006.01)

(52) U.S. Cl.
CPC ...... *A61M 5/31505* (2013.01); *A61M 5/3129* (2013.01); *A61M 5/3137* (2013.01); *A61M 5/3146* (2013.01); *A61M 5/31515* (2013.01); *A61M 5/31586* (2013.01); *A61M 2005/3109* (2013.01); *A61M 2005/3123* (2013.01); *A61M 2005/3139* (2013.01); *A61M 2005/31508* (2013.01)

(58) Field of Classification Search
CPC ............ A61M 5/3146; A61M 5/31515; A61M 5/31586; A61M 5/31505; A61M 5/3129; A61M 5/31501; A61M 2005/31508; A61M 5/31536; A61M 5/3137; A61M 5/31511

See application file for complete search history.

(56) References Cited

U.S. PATENT DOCUMENTS

| | | | |
|---|---|---|---|
| 2002/0114782 A1* | 8/2002 | Wolfe | A61K 9/0019 424/85.6 |
| 2014/0005610 A1* | 1/2014 | Kakiuchi | A61M 5/284 604/224 |
| 2014/0316334 A1* | 10/2014 | Holmqvist | A61M 5/31571 604/89 |
| 2015/0105734 A1* | 4/2015 | Bryant | A61M 5/31505 604/218 |
| 2017/0281872 A1* | 10/2017 | Guthart | A61M 5/31501 |

* cited by examiner

*Primary Examiner* — Matthew F Desanto
(74) *Attorney, Agent, or Firm* — Min Wei

(57) ABSTRACT

A pre-filled syringe for sterile medication fluid injection includes a syringe barrel with rotationally symmetric cylindrical bore, having a distal end and a proximal end; a syringe piston with rotationally symmetric external shape; a backstop mounted at the proximal end of the syringe barrel with an opening that is rotationally asymmetric about the axis through the syringe barrel; a push rod to move the syringe piston inside the syringe barrel, wherein at least one portion of the push rod is rotationally asymmetric about the axis through the syringe barrel, and upon rotation, the rotationally asymmetric portion of the push rod is aligned with the rotationally asymmetric opening of the backstop; and a seal component to cover the distal end of the syringe barrel.

6 Claims, 5 Drawing Sheets

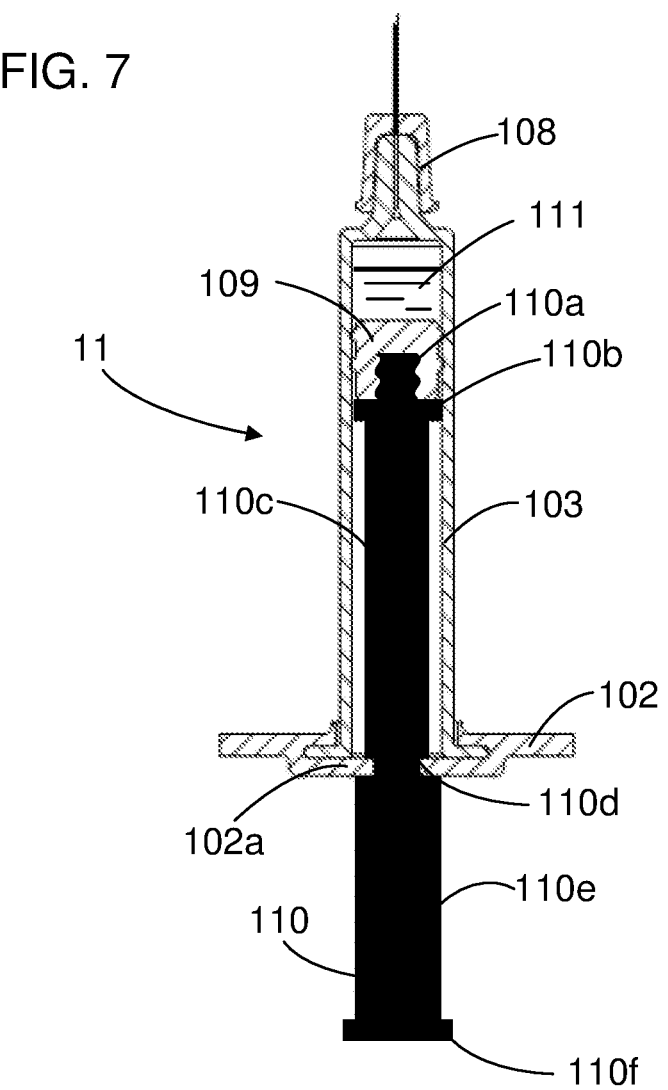

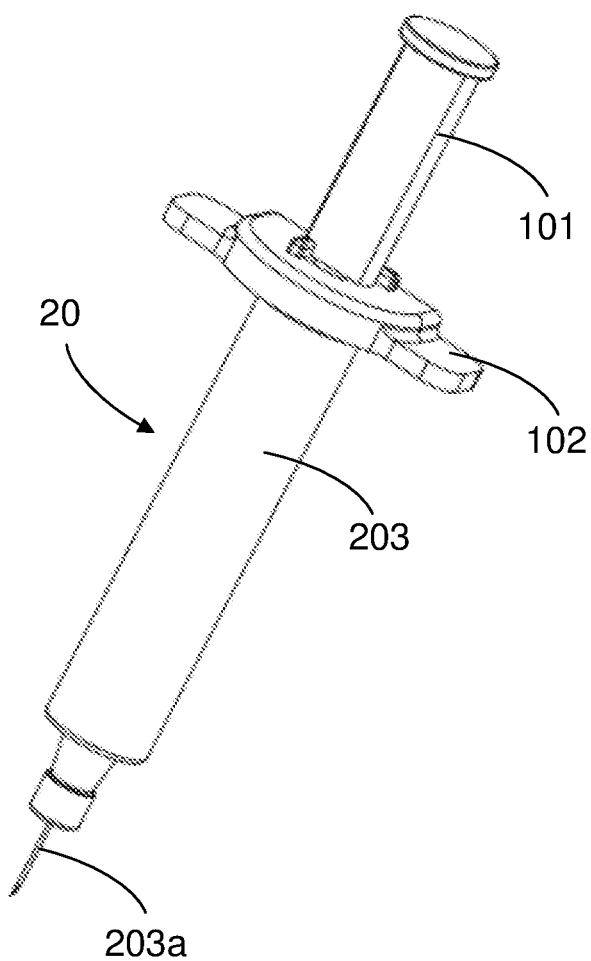

SYRINGE TYPE MEDICATION DELIVERY DEVICE

CROSS-REFERENCE TO RELATED APPLICATIONS

This application claims the benefit of U.S. Provisional Application Ser. No. 62/467,065, filed Mar. 3, 2017.

BACKGROUND OF THE INVENTION

The present invention pertains to medication delivery devices, and, in particular, to a syringe type injection device.

Currently, biologic drugs account for more than half of all therapeutic drug candidates in pharmaceutical development pipelines. These biologic drugs need to be delivered through the parenteral route. As the injectable drugs become more and more popular, medication delivery devices are expected to be widely used by patients and health care professionals. Pre-filled syringe is a current form of medication device mainly used for injectable drugs. For the pharmaceutical company, the advantages of pre-filled syringes are minimizing drug waste; increasing product life span and enhancing level of market share are some of driving market demand. For healthcare workers, pre-filled syringes are recognized as an efficient, reliable and convenient method for drug administration.

However, without improvement, the current pre-filled syringe isn't ideally designed for injections that need priming step to remove air bubble. The proper priming is even more important for small volume injection, for example, 0.1 mL or less for ophthalmic injection. In pre-filled syringe, sterile medication fluid filling and syringe piston (seal component) placement happen at the same end of the syringe, which cause air bubble trapped in the syringe container after dose filling. Air bubble(s) need to be removed before sterile medication fluid injection in order to achieve precise dose. When removing the air bubble or excess sterile medication fluid, it is possible to expel filled sterile medication fluid more than desired and then cause under dosing, without sufficient control mechanism. For example, Iucentis® (ranibizumab injection) 0.05 mL pre-filled syringe only have a dose mark on the syringe barrel for dose setting. Without better control mechanism, it is very easy for user to expel sterile medication fluid more than needed during the air bubble removal process (or priming process), which will lead to under dose for patients.

Moreover, there are some biological drug formulations (including cell and gene therapies) that have to be stored at frozen state to maintain stability over shelf time. For example, cell therapy products shall be stored at temperature lower than −120° C. During the freezing process, air bubble volume inside of pre-filled syringe will reduce. At the same time, liquid volume inside of pre-filled syringe will also expand/retract at different temperature. Consequently, syringe piston inside pre-filled syringe very likely slides along the axial of syringe barrel during the freezing process. The syringe piston movement will increase risk of sterility breach. Similarly, if the pre-filled syringe is shipped through air transportation, air pressure changes at different elevation levels can also cause the movement of syringe piston and then increase risk of sterility breach. While U.S. Pat. No. 9,220,631 discloses injection device design configuration preventing syringe piston from moving away from injection outlet, the design only prevent the syringe piston movement in one direction and the design can not prevent the syringe piston from moving toward to injection outlet. Therefore, U.S. Pat. No. 9,220,631 don't completely solve the plunger movement issue.

In summary, what is needed is an improvement upon current pre-filled syringe design to further utilize the medication delivery device in more application areas.

SUMMARY OF THE INVENTION

In one form thereof, the present invention provides a syringe type medication delivery device having a syringe barrel with a distal end and a proximal end, the distal end is meant to refer to the end of the medication delivery device where medication is delivered into the patient body, whereas the proximal end is meant to refer to the end opposite to the distal end along the longitudinal axis of the device body; a syringe piston (seal component); a push rod that is designed for delivering pre-set volume of sterile medication fluid or is able to lock the syringe piston in place before medication delivery; and a backstop working together with the push rod in this invention. The sterile medication fluid herein might be solution, suspension, emulation or other forms in fluid state.

One advantage of the present invention is that a target deliver volume is preset. The push rod will move a fixed distance to remove the air bubble and then stop before injection. The chance of expelling too much formulation during the air bubble removal is greatly reduce. Consequently, the risk of under dose is also greatly reduced.

Another advantage of the present invention is that syringe piston movement can be avoided during freezing process if the formulation content inside the pre-filled syringe needs to be frozen for stability purpose. Therefore, sterility of the formulation won't be adversely affected.

Another advantage of the present invention is that syringe piston movement can be avoided during air transportation or under other circumstances that cause air pressure change outside of the pre-filled syringe. Therefore, sterility of the formulation won't be adversely affected.

Still another advantage of the present invention is that the locked push rod design can be used for other type of pharmaceutical container, for example, pre-filled cartridge.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which:

FIG. 7 is a cross-sectional view of another configuration of the exemplary pre-filled syringe according to the invention.

FIG. 8 is a perspective view of an alternative pre-filled syringe according to the invention.

DETAILED DESCRIPTION OF THE INVENTION

Figure 1:
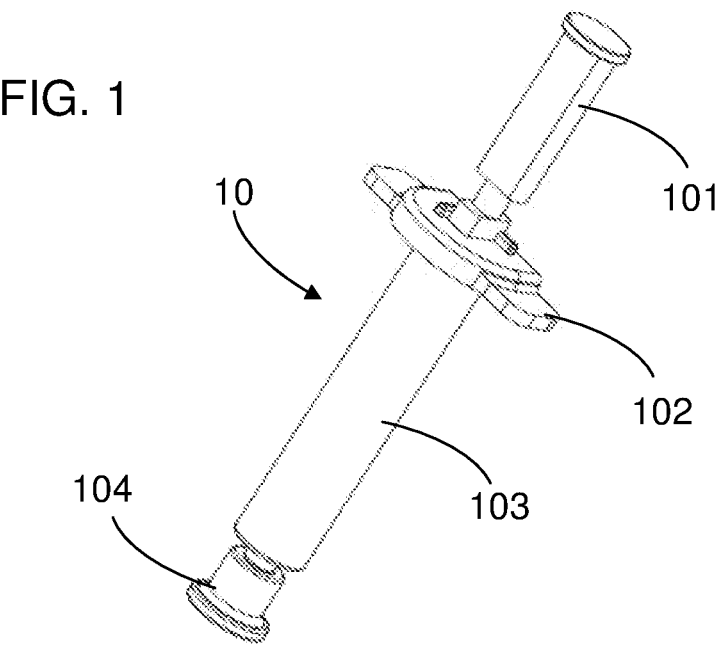
FIG. 1 is a perspective view of an exemplary pre-filled syringe according to the invention.
Figure 2:
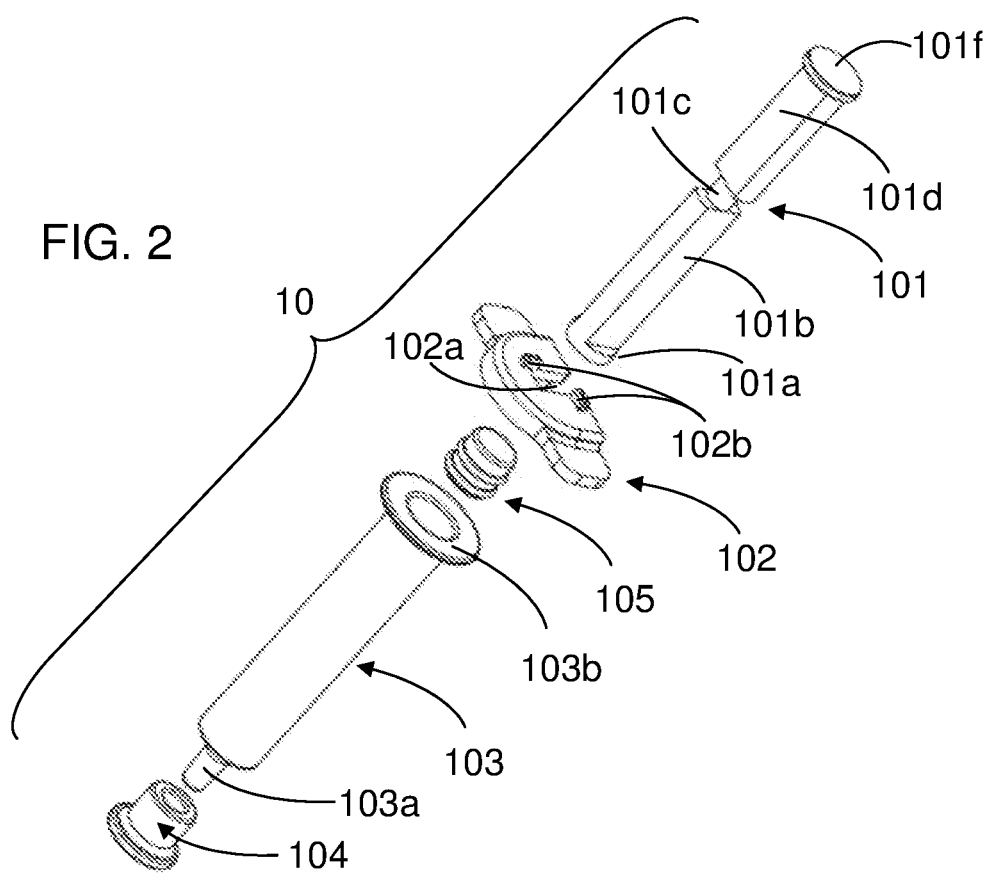
FIG. 2 is an exploded view of the exemplary pre-filled syringe according to the invention.
Figure 3:
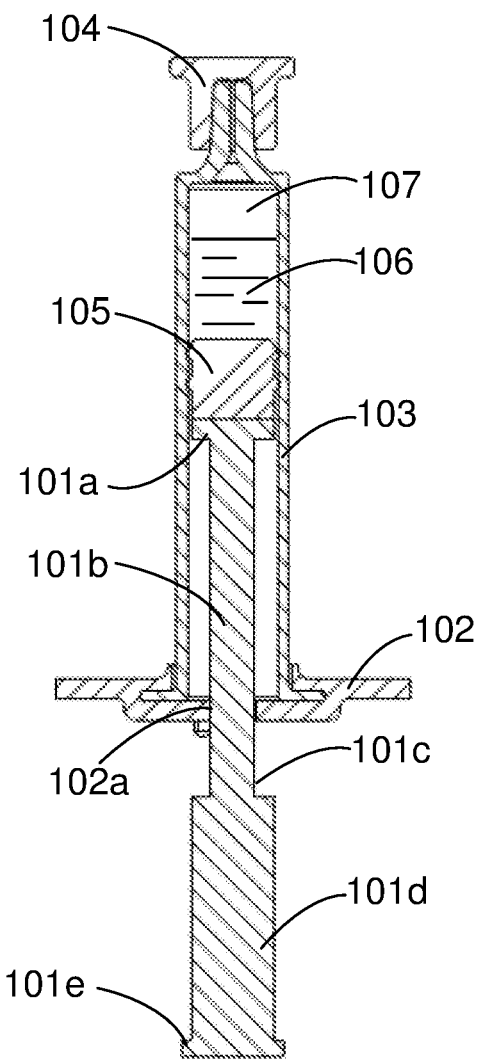
FIG. 3-6 show cross-sectional views of the exemplary pre-filled syringe at different operational steps, according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as medication, into a patient. Initially it may be convenient to define that, the term "distal end" is meant to refer to the end of the pre-filled syringe where medication is delivered into the patient, whereas the term "proximal end" is meant to refer to the end opposite to the "distal end" along the longitudinal axis of the pre-filled syringe body. The words "upper", "lower", "right" and "left" designate directions in the drawings to which reference is made. The words "inward" and "outward" refer to directions toward and away from, respectively.

FIGS. 1-6 illustrate the construction and function mechanism of an exemplary pre-filled syringe 10 according to the invention. With reference to FIG. 1, in this pre-filled syringe 10, a pre-filled syringe barrel 103, as medication container, can be made of either glass or plastic materials. The syringe barrel 103 may be a substantially rotationally symmetric cylindrical shell, or may include a substantially rotationally symmetric cylindrical bore with a non circular outer shape. The syringe barrel 103 is of a generally standard design with a luer lock feature 103a at its distal end which is in fluid communication with the sterile medication fluid contents of the syringe barrel 103. The syringe piston 105 may be made from rubber, silicone or other suitable resiliently deformable material. The external shape of syringe piston 105 may be substantially rotationally symmetric about an axis through the syringe piston 105. The syringe piston 105 may include one or more circumferential ribs around an outer surface of the piston, the syringe piston 105 and ribs being dimensioned such that the ribs form a substantially fluid tight seal with an internal surface of the syringe barrel. The front surface of the syringe piston 105 may be any suitable shape, for example substantially planar, substantially conical or of a domed shape. Sterile medication fluid 106 and air bubble 107 inside of the pre-filled syringe barrel 103 are sealed by the syringe piston 105 and a seal component 104. The volume of sterile medication fluid 106 may be 0.1 mL or less. The seal component 104 may be elastomeric or plastic luer lock cap, which is configured to maintain sterility for the medication content. The seal component 104 is placed at the distal end of the syringe barrel 103.

The pre-filled syringe 10 may include a backstop 102 arranged at a proximal end of the syringe barrel 103. The backstop 102 may be removable from the pre-filled syringe 10. If the syringe barrel 103 includes terminal flange 103b at the proximal end, the backstop may be configured to substantially sandwich terminal flange 103b of the syringe barrel 103 as this prevent movement of the backstop 102 in directions parallel to the syringe barrel axis. On the backstop 102, there is an opening slot 102a that is substantially rotationally asymmetric about the axis through the syringe barrel 103. There may be also stopping feature 102b along the edge of the oriented opening slot 102a.

Figure 4:
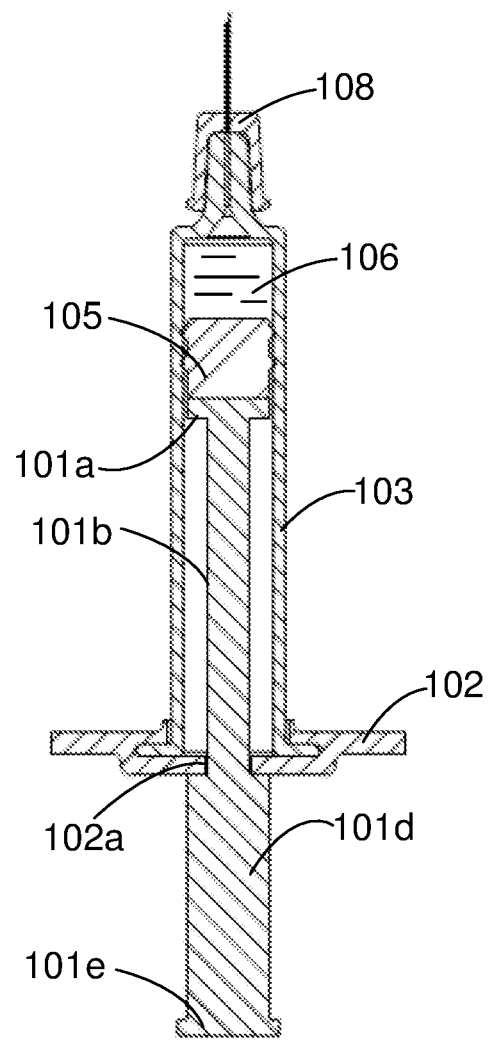
Figure 5:
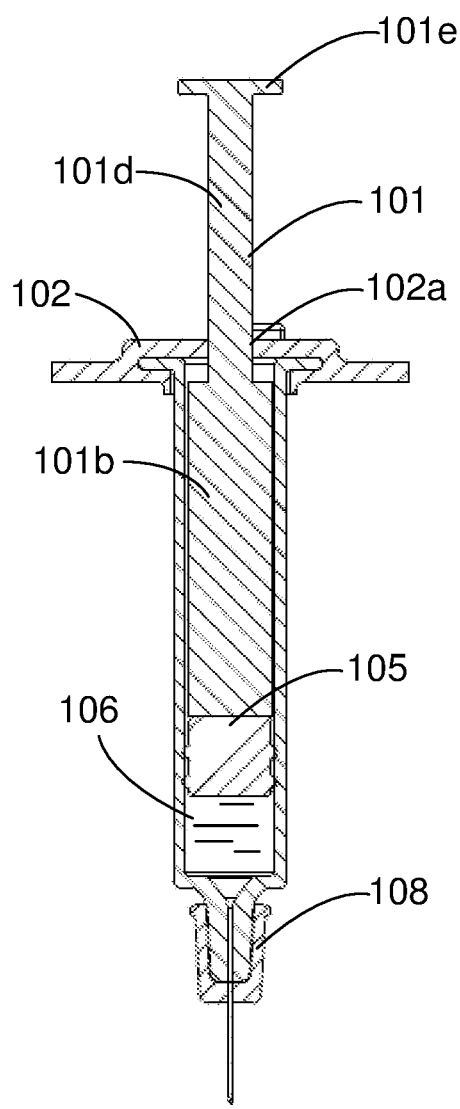
Figure 6:
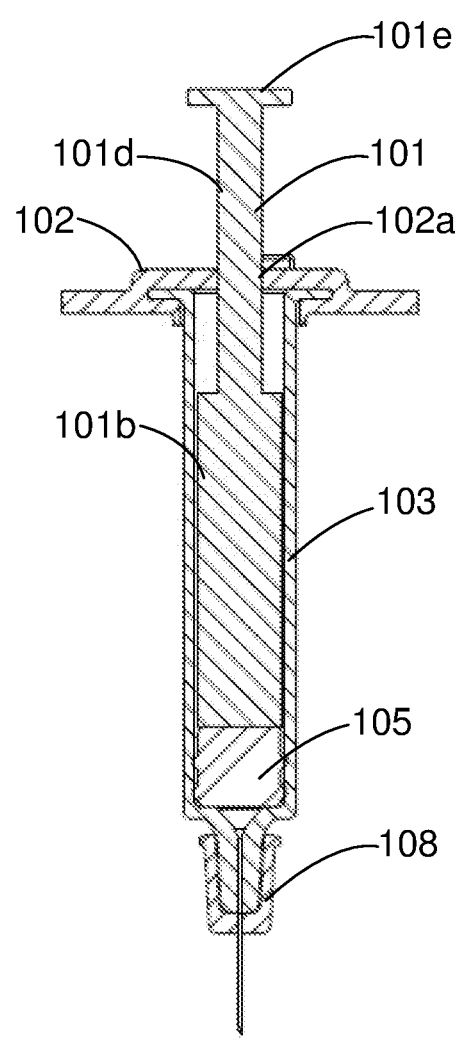

A push rod 101 is provided to move the syringe piston 105. The push rod 101 comprises a syringe piston contact portion 101a, a first push rod body portion 101b, a substantially cylindrical portion 101c, a second push rod body portion 101d and a user contact portion 101e. The user contact portion 101e may comprise a substantially disc shaped portion. Both the first 101b and second 101d push rod body portions may be substantially rotationally asymmetric about the axis through the syringe barrel 103. As an example illustrated herein, both the first 101b and second 101d push rod body portions have two flat panels. The flat panels on push rod portion 101b and 101d are perpendicular to each other along the axis of syringe barrel 103. Before use, the first push rob portion 101b is aligned with the opening slot 102a on the backstop 102 (FIG. 3) so that the push rob 101 can be pushed toward to the distal end of the syringe barrel. To ensure that an exact and pre-determined dosage is administered to the patient, a priming step is required. This priming step allows the physician to expel excess sterile medication fluid and any air bubbles from the syringe. Before the priming process, user may remove the seal component 104 and then install a luer lock needle 108. During priming, user has the needle tip pointing up and moves the air bubble 107 to the top of the syringe barrel 103 (for example, gently tapping the syringe with finger until the bubbles rise to the top). Then, the push rod 101 is pushed upward in order to remove the air bubble 107 and excess sterile medication fluid, until push rod 101 stops when the second rod body portion 101d is landed on the opening slot 102a on the backstop 102 (FIG. 4). By this way, it is prevented to expel more sterile medication fluid than desired, and the possibility of under dosing is removed. To inject sterile medication fluid to patient, user rotates the push rod 101 by 90 degree to align the second push rod portion 101d with the opening slot 102a (FIG. 5) so that the push rod 101 can be pushed toward to the distal end of the syringe barrel 103, while the cylindrical portion 101c of push rod 101 is placed inside the opening slot 102a. The rotation of push rod is assisted by the cylindrical portion 101c on the push rod 101. Also, the stopping features 102b on the backstop 102 help the alignment between the second push rod portion 101d and the opening slot 102a. During sterile medication fluid injection, user further pushes the push rod 101 to inject the preset medication dose into injection site (FIG. 6).

FIG. 7 shows a cross-sectional view of another configuration (pre-filled syringe 11) of the exemplary pre-filled syringe 10 according to the invention. In the pre-filled syringe 11, the rear surface of syringe piston 109 may include a substantially central recess. Such a central recess could be used to connect a push rod 110 to the syringe piston 109 using a thread connection 110a on the push rod 110 or a snap fit feature in a known manner. The sterile medication fluid 111 may be in frozen state during storage. The syringe piston 109 may be rotatable and substantially rotationally symmetric about an axis through the syringe piston 109. The push rod 110 also comprises a substantially cylindrical first rod body portion 110c, a substantially cylindrical portion 110d, a second rod body portion 110e and a user contact portion 110f. The second rod body portion 110e may be substantially rotationally asymmetric about the axis through the syringe barrel 103. As an example illustrated herein, the second rod body portion 110e may comprise two flat side panels. Before use, the flat panels on the second rod body portion 110e are rotationally offset from the orientation of the opening slot 102a on the backstop 102 (for example, offset by 90 degree) in order to lock the push rod in place before use. This design only allow push rod to move distally during use. As an alternative to the push rod 110, both the first 101c and second 101e rod body portions have two flat panels and the flat panels on the two push rod portions may be parallel. Before use, the flat panels on the two push rod portions are all rotationally 90 degree offset from the orientation of the opening slot 102a on the backstop 102 in order to lock the push rod in place before use. This alternative design allows push rod to move both distally and proximally. Other similar known matters for restraining the push rod may also be applied. During the sterile medication fluid injection, user may rotate the push rod 110 to align the second rod body portion 110e with the opening slot 102a so that the push rod 110 can be pushed toward to the distal end of the syringe barrel 103 for sterile medication fluid injection. Restriction of the movement of the push rod along the syringe barrel axis can help to maintain sterility during freezing process, terminal sterilization operations, air transportation or other operations in which the air pressure within the variable volume chamber or outside the chamber may change. During such operations any gas trapped within the variable volume chamber, or bubbles that may form in a liquid therein, may change in volume and thereby cause the syringe piston to move. Movement of the syringe piston could result in the breaching of a sterility zone created by the syringe piston. This is particularly important for low volume syringes where there are much lower tolerances in the component sizes and less flexibility in the stopper. The term sterility zone as used herein is used to refer to the area within the syringe that is sealed by the syringe piston. This may be the area between a seal of the syringe piston, for example a circumferential rib, closest to the outlet and a seal of the stopper, for example a circumferential rib, furthest from the outlet. The distance between these two seals defines the sterility zone of the syringe piston since the syringe piston is installed into the syringe barrel in a sterile environment.

FIG. 8 shows a perspective view of a pre-filled syringe 20 according to the invention. In the pre-filled syringe 20, the medication outflow pathway is a hollow needle 203a. Herein, the needle 203a is staked in the syringe body 203. A seal component (not shown), needle shield, is used to cover the needle 203a to maintain sterility of medication content before use.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A pre-filled syringe containing sterile medication fluid for injection, the pre-filled syringe comprising:
    a syringe barrel with cylindrical bore, having a distal end and a proximal end;
    a syringe piston to seal the sterile medication fluid in the syringe barrel;
    a backstop having a rotationally asymmetric opening slot, mounted at the proximal end of the syringe barrel;
    a seal component to cover the distal end of the syringe barrel; and
    a push rod to move the syringe piston inside the syringe barrel, having a first flat panel portion with a proximal end, a second a flat panel portion with a distal end, and a connecting portion connecting the proximal end of the first flat panel portion and the distal end of the second flat panel portions along the push rod; wherein the first flat panel portion of the push rod has a rotationally asymmetric cross-section; the second flat panel portion of the push rod has substantially the same rotationally asymmetric cross-section and orientation on the push rod as the first flat panel portion of the push rod; the connecting portion of the push rod has uniform diameter with a substantially circular cross-section running through its entire length; and the first flat panel portion, second flat panel portion, connecting portion and backstop are configured to lock the push rod in place.

2. The pre-filled syringe as in claim 1, wherein volume of the sterile medication fluid is less than 0.1 mL.

3. The pre-filled syringe as in claim 1, wherein the sterile medication fluid is in frozen state during storage.

4. The pre-filled syringe as in claim 1, wherein there is at least one air bubble between the syringe piston and the seal component.

5. The pre-filled syringe as in claim 1, wherein wherein the seal component is a tip cap for luer lock.

6. The pre-filled syringe as in claim 1, further comprising a hollow needle placed at the distal end of the syringe barrel, wherein the seal component is a needle shield.

* * * * *